(12) United States Patent
Manning et al.

(10) Patent No.: US 7,493,156 B2
(45) Date of Patent: Feb. 17, 2009

(54) STEERABLE GUIDE CATHETER WITH PRE-SHAPED ROTATABLE SHAFT

(75) Inventors: Frank E. Manning, Valley Center, CA (US); Charles R. Peterson, Murrieta, CA (US); Howard P. Graham, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/041,911

(22) Filed: Jan. 7, 2002

(65) Prior Publication Data
US 2003/0130598 A1 Jul. 10, 2003

(51) Int. Cl.
*A61B 6/00* (2006.01)
*A61B 5/00* (2006.01)
*A61M 25/00* (2006.01)

(52) U.S. Cl. .................... 600/434; 600/561; 600/585
(58) Field of Classification Search ................ 600/433, 600/434, 435, 585; 604/164.03, 164.05, 604/164.13, 171
See application file for complete search history.

(56) References Cited

U.S. PATENT DOCUMENTS

| | | | | |
|---|---|---|---|---|
| 4,586,923 A | * | 5/1986 | Gould et al. ............. | 604/95.04 |
| 5,409,469 A | * | 4/1995 | Schaerf .................... | 604/524 |
| 5,462,527 A | * | 10/1995 | Stevens-Wright et al. ... | 604/528 |
| 6,083,170 A | * | 7/2000 | Ben-Haim ................ | 600/463 |
| 6,408,214 B1 | * | 6/2002 | Williams et al. .......... | 607/122 |
| 6,485,455 B1 | * | 11/2002 | Thompson et al. ....... | 604/95.04 |
| 6,533,770 B1 | * | 3/2003 | Lepulu et al. ............ | 604/524 |
| 6,574,512 B1 | * | 6/2003 | Zhang et al. ............. | 607/122 |
| 6,592,581 B2 | * | 7/2003 | Bowe ..................... | 606/41 |
| 6,638,268 B2 | * | 10/2003 | Niazi ...................... | 604/528 |
| 2001/0039413 A1 | * | 11/2001 | Bowe ..................... | 604/532 |

* cited by examiner

*Primary Examiner*—Max Hindenburg
*Assistant Examiner*—Jonathan M Foreman
(74) *Attorney, Agent, or Firm*—Hollingsworth & Funk, LLC (57) ABSTRACT

A guide catheter employs a retractable inner sheath movably disposed within an open lumen of an outer sheath. The inner sheath includes a pre-formed distal end and an open lumen adapted to receive a payload. The inner sheath is translatable and rotatable relative to the outer sheath. The inner sheath conforms to the outer sheath shape until it is distally extended beyond the outer sheath. The outer sheath contains a steering tendon that can be used to adjustably deflect the outer sheath. The guide catheter further includes a proximally attached guide handle. A steering handle can be pivotably connected to the guide handle. The steering handle is connected to the steering tendon and can apply a tensile force to the steering tendon for adjustably deflecting the outer sheath. A catheter according to the present invention provides an improved system for locating and cannulating cardiac venous structures, particularly the coronary sinus via the right atrium.

34 Claims, 6 Drawing Sheets

Section 1-1
Fig 3B

STEERABLE GUIDE CATHETER WITH PRE-SHAPED ROTATABLE SHAFT

FIELD OF THE INVENTION

The invention relates generally to guide catheters, and more particularly to dual-sheath, telescoping guide catheters having a steerable outer sheath and pre-formed inner sheath used to locate and cannulate the coronary sinus of a patient's heart.

BACKGROUND OF THE INVENTION

Guiding catheters are instruments that allow a physician to locate and cannulate vessels in a patient's heart for preforming various medical procedures, including venography and implanting of cardiac pacing devices. Cannulating heart vessels requires navigating a small diameter, flexible guide through the convoluted vasculature into a heart chamber, and then into a destination heart vessel. Once the destination heart vessel is reached, the catheter acts as a conduit for insertion of payloads into the vessel.

A commonly accessed destination vessel for cardiac pacing lead insertion is the coronary sinus. A pre-shaped guiding catheter is typically used to blindly locate the coronary sinus ostium. This endeavor, however, is complicated by the fact that the location of the coronary sinus ostium may vary appreciably from one patient to another, especially among patients with diseased hearts. Oftentimes, the clinician is entirely unable to locate the coronary sinus ostium using the guiding catheter, and must resort to finding the ostium by "mapping" (interpreting localized bipolar waveforms) using an electrophysiological (EP) catheter and an ECG monitor. After the ostium is located, the guiding catheter is typically used to inject radiographic contrast media into the coronary sinus to highlight the associated venous system, and then a pacing lead is installed within one of the coronary branches.

Complicating this scenario is the dynamic structural deformation of the heart chambers that occurs from normal cardiac activity during the procedure. This further increases the difficulty of guiding a catheter to its destination. Presently, a considerable amount of time is often spent by the physician when manipulating such catheters within cardiac structures, such as the right atrium, simply trying to locate an anatomical feature of interest, such as the coronary sinus ostium.

Guiding catheter systems are typically configured with a profile that is optimized for the intended method of access. In the case of accessing the coronary sinus via the right atrium, a catheter with a distal contour including a relatively sharp bend will point the catheter towards the likely location of the coronary sinus once the right atrium is reached. The contours of pre-shaped guiding catheters are generally fixed, and this is typically achieved in production by constraining the distal end within a shaping fixture while warming them until they assume the intended shape (i.e., by "heat setting" their polymer shaft).

A fixed shape catheter is adequate in many cases where the pathway is not significantly convoluted and the pathway does not deviate significantly between patients. In situations where structural anomalies or significant variations exist, use of a fixed shape catheter may require that the clinician stock multiple size and shapes of catheters to account for potential variations. Fixed shape catheters may require a time consuming trial and error process of inserting and removing different shapes until the destination vessel is successfully accessed.

There is a need for an improved guide catheter for accessing heart vessels that can dynamically account for anatomical variations and defects associated with the destination structures. The present invention fulfills these and other needs, and addresses other deficiencies of prior art implementations and techniques.

SUMMARY OF THE INVENTION

The present invention is directed to a guide catheter for cannulating a vessel of a patient's heart. According to one embodiment of the invention, a guide catheter includes an outer sheath having an open lumen and a pre-shaped distal end. An inner sheath having an open lumen is disposed within the open lumen of the outer sheath. The inner sheath is axially rotatable and longitudinally translatable relative to the outer sheath. The pre-shaped distal of the inner sheath conforms to a shape of the outer sheath when the inner sheath is retracted, and the distal end of the inner sheath assumes a pre-formed shape when the distal end of the inner sheath is extended beyond the distal end of the outer sheath. A steering tendon is disposed along the outer sheath. A distal end of the steering tendon is connected to a distal tip of the outer sheath. A guide handle is connected to a proximal end of the outer sheath. A steering mechanism is disposed on the guide handle. The steering mechanism is connected to a proximal end of the steering tendon. The steering mechanism provides a pulling force on the steering tendon to adjustably change an angle of the pre-shaped distal end of the outer sheath.

In one configuration, the steering mechanism includes a steering handle pivotably connected to the guide handle. In another aspect, the outer sheath may further include at least one longitudinally displaced pre-stress line extending from the proximal end to the distal tip of the outer sheath. Similarly, the inner sheath may further include at least one longitudinally displaced pre-stress line extending from a proximal end to a distal tip of the inner sheath.

The guide catheter may be configured with at least one electrode on the distal end of one the inner sheath. At least one electrical conductor can be coupled to the electrode(s), the conductor(s) being disposed within the inner sheath. Similarly, another configuration includes at least one electrode on the pre-shaped distal end of the outer sheath, with at least one electrical conductor coupled to the electrode(s), the conductor(s) disposed within the outer sheath. The guide catheter may also include an occlusion device connected to the distal end of the inner sheath. An occlusion device may also be connected to the pre-shaped distal end of the outer sheath. In another configuration, at least one pressure sensing device is connected to the distal end of the inner sheath. At least one electrical conductor is coupled to the pressure sensing device(s), the conductor(s) being disposed within the inner sheath. At least one pressure sensing device can also be connected to the pre-shaped distal end of the outer sheath. At least one electrical conductor is coupled to the pressure sensing device(s), the conductor(s) being disposed within the inner sheath.

In a particularly useful configuration of the guide catheter, the pre-shaped distal end of the outer sheath includes a substantially straight section at the distal tip of the outer sheath with a length of about 1 cm to about 5 cm. Proximally adjacent the straight section is a substantially circular curve having a bend radius ranging from about 0 degrees to about 180 degrees and a bend radius ranging from about 1 cm to about 7 cm.

The inner sheath may also include a substantially straight section at the distal tip having length of about 0.5 cm to about 4.0 cm. Proximally adjacent the straight section is a substantially circular curve. The curve has a bend radius ranging from about 0 degrees to about 150 degrees and a bend radius ranging from about 1 cm to about 5 cm.

The steering tendon may be disposed on an outer surface of the outer sheath. Alternatively, the steering tendon may be disposed within the open lumen of the outer sheath. In yet another configuration, the outer sheath may further include a second lumen, and the steering tendon is disposed within the second lumen.

In another embodiment of the present invention, a method of inserting a payload into the coronary sinus of a patient's heart involves providing a guide catheter. The guide catheter includes an outer sheath having an open lumen and a pre-shaped distal end. An inner sheath having an open lumen and a pre-shaped distal end is disposed within the open lumen of the outer sheath. The inner sheath is axially rotatable and longitudinally translatable relative to the outer sheath. The pre-shaped distal of the inner sheath conforms to a shape of the outer sheath when the inner sheath is retracted, and the distal end of the inner sheath assumes a pre-formed shape when the distal end of the inner sheath is extended beyond the distal end of the outer sheath. A steering tendon is disposed along the outer sheath. A distal end of the steering tendon is connected to a distal tip of the outer sheath. A guide handle is connected to a proximal end of the outer sheath. A steering mechanism is disposed on the guide handle. The steering mechanism is connected to a proximal end of the steering tendon. The steering mechanism provides a pulling force on the steering tendon to adjustably change an angle of the pre-shaped distal end of the outer sheath.

The method further involves inserting a distal end of the catheter through the patient's right atrium via an access vessel. The inner sheath is distally extended from the outer sheath, the distal end of the inner sheath assuming a pre-formed shape upon extension from the outer sheath. A pulling force is provided on the steering tendon to adjustably change an angle of the pre-shaped distal end of the outer sheath, the inner sheath axially rotated relative to the outer sheath, and the inner sheath longitudinally translated relative to the outer sheath to direct the distal end of the inner sheath for finding and cannulating the patient's coronary sinus. The payload is then advanced through the open lumen of the inner sheath until the payload is inserted into the patient's coronary sinus.

Another embodiment of the method involves distally advancing the outer sheath over the inner sheath to seat the outer sheath in the coronary sinus after finding and cannulating the patient's coronary sinus. The inner sheath is proximally retracted to remove the inner sheath from the outer sheath. The payload is then advanced through the open lumen of the outer sheath to insert the payload into the patient's coronary sinus.

In one aspect of the previously described methods, the payload includes a pacing lead. The methods may also include injecting a contrast media into the open lumen of the inner sheath for venography after finding and cannulating the patient's coronary sinus. In one configuration, the outer sheath of the catheter further comprises at least one longitudinally displaced pre-stress line extending from the proximal end to the distal tip of the outer sheath. In this case, the methods further comprise splitting the outer sheath while retracting the outer sheath in a proximal direction to remove the outer sheath after inserting the payload through the open lumen of the inner or outer sheaths.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

Figure 1:
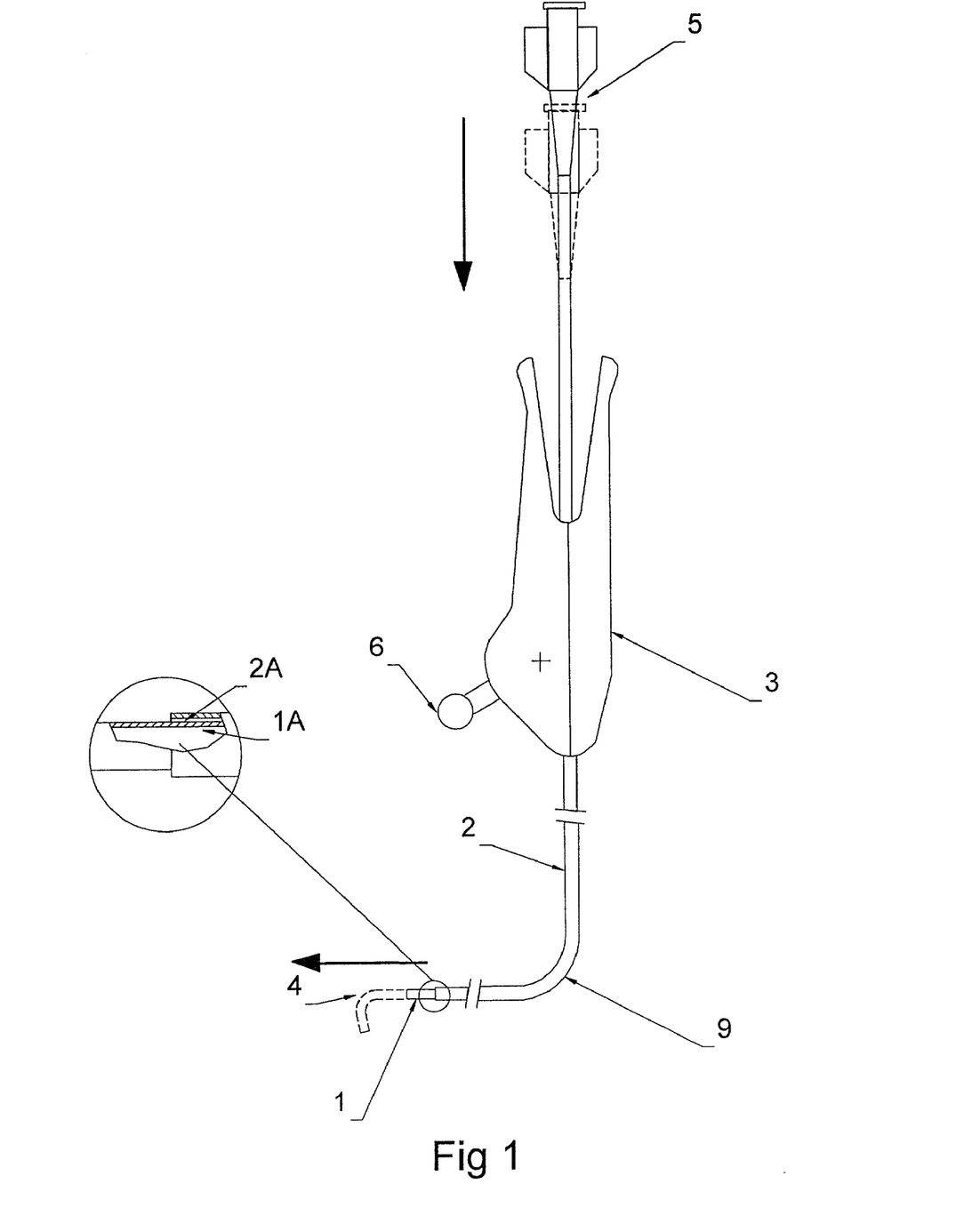
FIG. 1 is an external view of a catheter embodying features of the present invention and illustrating longitudinal translation of an inner sheath relative to an outer sheath.

With reference to FIG. 1, a guide catheter is shown embodying features of the present invention. The guide catheter includes an inner sheath 1, an outer sheath 2, and a guide handle 3. The guide handle 3 is connected to a proximal end of the outer sheath 2. The guide handle 3 can include a homeostasis device that provides a seal between the inner and outer sheaths 1, 2. The outer sheath 2 contains an open lumen 2A, and the outer sheath 2 is typically elongated and flexible. The outer sheath 2 is also adjustably deflectable at a distal end. The inner sheath 1 is movably disposed within the open lumen 2A of the outer sheath 2 such that the inner sheath 1 can translate longitudinally and rotate axially within the outer sheath 2.

The inner sheath 1 is typically more flexible than the outer sheath and includes a pre-formed distal shape 4. The more flexible inner sheath 1 conforms to the shape of the outer sheath 2 when a substantial portion of the inner sheath's distal end is contained within the outer sheath 2. When the inner sheath 1 is sufficiently extended, the distal end of the inner sheath 1 assumes its pre-formed distal shape 4, as indicated by phantom lines in FIG. 1.

The inner sheath 1 can be formed of a polymeric tube. Pebax is a polymer typically used in this application, although other materials such as nylon and PVC may be employed. Constructing the inner sheath 1 from a multi-layered tube having a metallic braid may be desirable in some applications where greater stiffness is required. The pre-formed distal shape 4 can be thermoset during manufacture of the inner sheath 1.

The inner sheath 1 has an open lumen 1A that can receive a payload. An inner lubricous lining made of a material such as PTFE can be provided within the open lumen 1A. The lubricious liner helps to ease advancement of payloads through the open lumen 1A. An inner sheath 1 used in coronary sinus cannulation procedures may have an inner lumen diameter of about 0.030 inches to about 0.100 inches, depending on the size of payloads and/or guide members that are intended to pass through or otherwise be disposed within the open lumen 1A.

The ability of the inner sheath 1 to assume a pre-formed distal shape 4 upon inner sheath extension is advantageous for accessing vessels within a patient's heart. For example, when accessing the patient's coronary sinus, a commonly traversed pathway is through a percutaneous access vessel such as the left subclavian, then through the superior vena cava and into the right atrium of the heart. This pathway is a relatively large, smooth curve, and outer sheath 2 can be shaped to accommodate the pathway. The inner sheath 1 can be retracted within the outer sheath 2 while the guide catheter is being advanced through the pathway, allowing the guide catheter to substantially assume the shape of the outer sheath 2.

Once the distal end of the catheter has entered the right atrium, a relatively sharp transition is desirable to access the coronary sinus ostium. The inner sheath 1 can now be extended to provide such a transition. Extension of the inner sheath 1 past the distal tip of the outer sheath 2 allows the distal end of the inner sheath 1 to assume its pre-formed distal shape 4. The pre-formed distal shape 4 can have dimensions that are optimized for locating the coronary sinus ostium, in this example. Axial rotation and longitudinal extension of the inner sheath 1 within the outer sheath 2 beneficially allows the distal end of the inner sheath 1 to account for variations within the right atrium while searching for the ostium.

Figure 2:
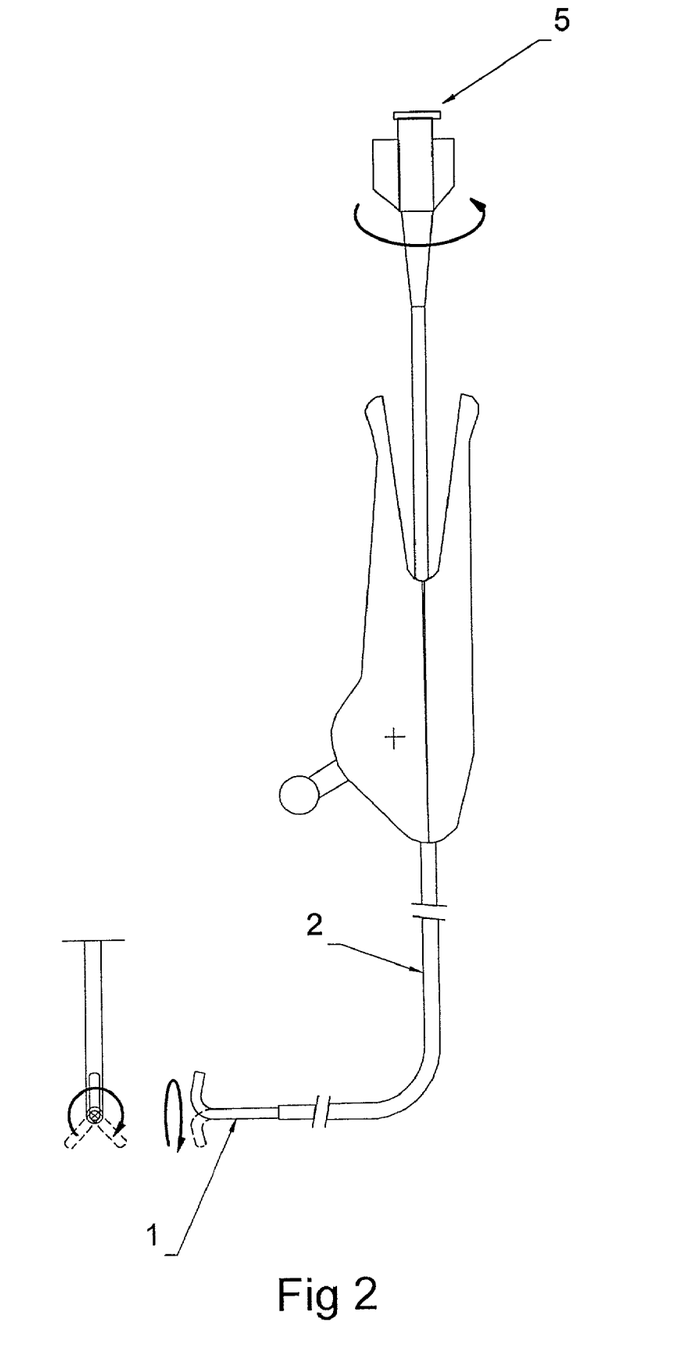
FIG. 2 is an external view of the catheter shown in FIG. 1 illustrating the inner sheath rotating within the outer sheath.

FIG. 2 illustrates the maneuverability provided by the rotatable inner sheath 1. The inner sheath 1 is axially rotatable within the outer sheath 2. Rotation of the inner sheath 1 is typically performed by grasping a proximal section of the inner sheath 1 and applying a torque to the inner sheath 1 while restraining the outer sheath 2. To assist in applying a torque, an attachment may be provided on the proximal end of the inner sheath 1, such as a wing luer 5, shown in FIG. 2. The curved arrows in FIG. 2 show the effect on the distal end of the inner sheath 1 caused by rotating the wing luer 5. Phantom lines at the distal end of the inner sheath 1 illustrate various rotated orientations of the inner sheath 1.

Figures 3A, 3B:
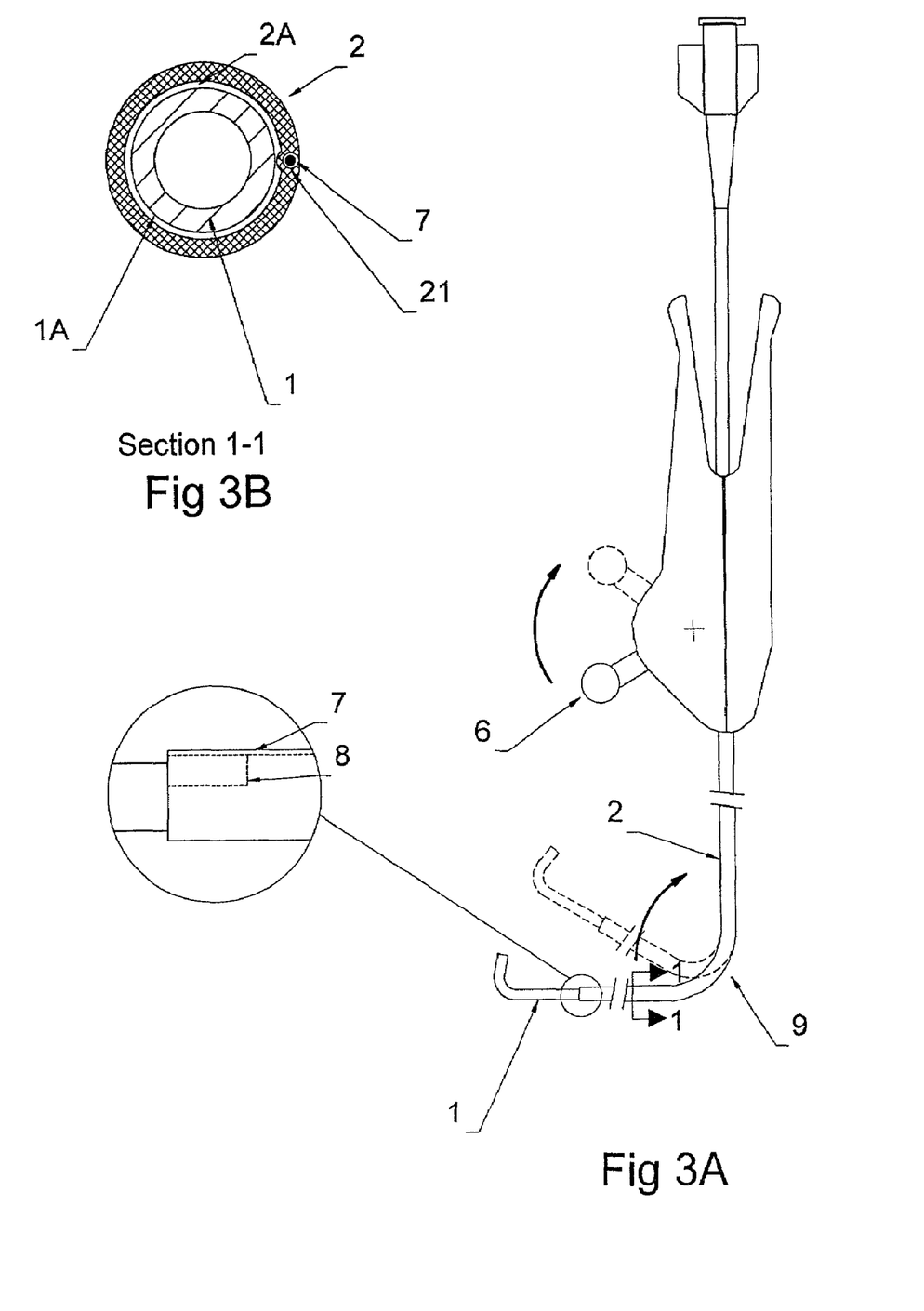
FIG. 3A is an external view of the catheter shown in FIG. 1 further illustrating a deflection of a pre-shaped distal end of the outer sheath
FIG. 3B is cross section view of Section 1-1 from FIG. 3A.

To provide further advantages with respect to accessing vessels within a heart chamber, the outer sheath 2 is adjustably deflectable. Referring to FIG. 3A, the deflectability of the outer sheath 2 is illustrated. The guide catheter includes a steering tendon 7 disposed within the outer sheath 2. The steering tendon 7 is attached to the distal end of the outer sheath 2, as shown in the detail drawing of FIG. 3A. In one configuration, the steering tendon 7 is attached by bonding or embedding a semicircular plate 8 near the outer sheath distal tip. The steering tendon 7 is fixably attached to the semicircular plate 8. Applying a tensile force on the proximal end of the steering tendon 7 changes a shape of the deflects the distal tip of the outer sheath 2.

A steering handle 6 may be attached to the guide handle 3 to enable adjustably applying a tensile force to the steering tendon 7. The steering handle 6 is typically pivotably mounted on the guide handle 3, and may include a friction or lock mechanism to hold the steering handle 6 at a fixed position.

To aid in the action of the steering tendon 7, the outer sheath 2 may include a pre-formed distal end 9. The pre-formed distal end 9 can be optimally shaped for advancement through heart chambers or intended venous pathways. The pre-formed distal end 9 may also determine the deflection point of the outer sheath 2 upon application of a tensile force to the steering tendon 7.

As shown in FIG. 3A, the outer sheath 2 has an initial shape at the pre-formed distal end 9. The direction of motion of the outer sheath 2 as it is deflected by the steering tendon 7 and steering handle 6 is indicated by the bold arrows. The deflected positions of the steering handle 6 and outer sheath 2 are indicated in phantom lines. The steering tendon 7 affects a bend angle and a bend radius of the pre-formed distal end 9, thereby enabling deflection of a distal tip of the guide catheter.

The outer sheath 2 may be formed of a polymeric tube similar to the inner sheath 1. The outer sheath 2 is typically stiffer than the inner sheath 1, and may benefit from a multi-layer construction that includes a metallic braid or coil. An inner lubricous lining made of PTFE or equivalent material can be provided within the outer sheath lumen 2A to reduce friction between the inner and outer sheaths 1, 2. The steering tendon 7 can be disposed within the outer sheath lumen 2A. The steering tendon 7 can also be disposed along an outer surface of the outer sheath 2. Alternatively, the outer sheath 2 can contain a second lumen 21 as seen in FIG. 3B. The steering tendon 7 is deployed within the second lumen 21. The steering tendon 7 may be formed of a metallic wire or ribbon, although other tensile members such as a high strength polymer fiber can also be employed with similar results.

A catheter embodying features of the present invention is particularly useful in applications such as implanting pacing and defibrillation leads into heart vessels. This procedure is illustrated FIG. 4. In such an application, the distal end of the catheter is typically introduced through a percutaneous access point 10, such as in the left cephalic vein or left subclavian vein. The inner sheath 1 can be retracted within the outer sheath 2 while the catheter is advanced through the access vessel into to the heart. As shown this example the catheter advances through the superior vena cava into the right atrium 11. In some cases, a guide wire 13 may be inserted through the venous pathway before the catheter is introduced, and the catheter then advanced over the guide wire 13 into the right atrium.

Figure 4:
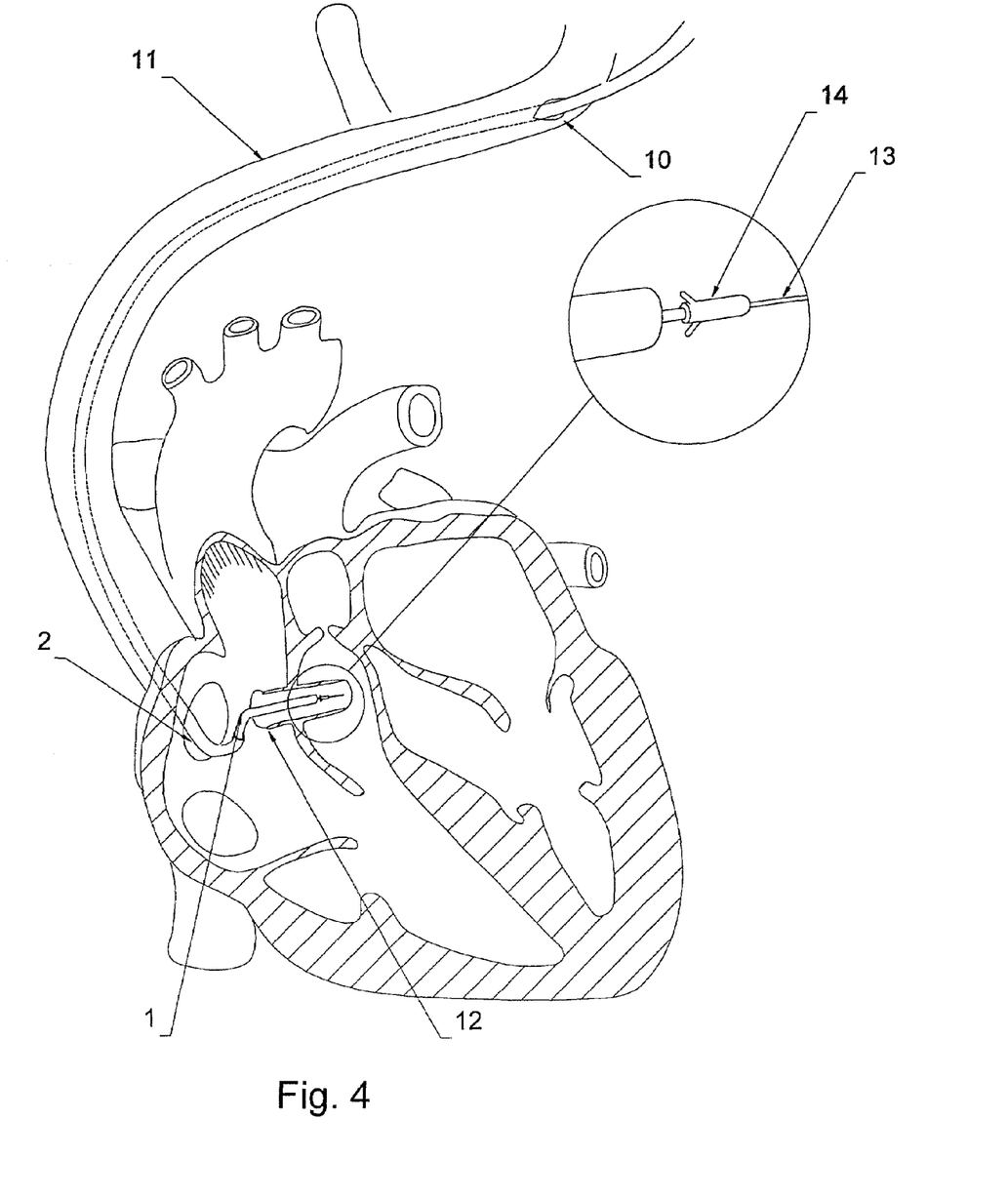
FIG. 4 is a cut-away view of a patient's heart, showing a catheter embodying features of the present invention deployed within the heart.

Once the distal tip of the outer sheath 2 has reached the right atrium, the inner sheath 1 can be extended. The inner sheath 1 is extended and rotated to locate the coronary sinus ostium 12. Additional assistance in finding the ostium 12 is provided by deflecting the outer sheath 2 via the steering tendon 7. Once the inner sheath 1 has located the ostium 12, the inner sheath 1 can be advanced as far as required into the coronary sinus.

If a guide wire 13 was introduced prior to inserting the catheter, the guide wire 13 can be advanced through the inner sheath 1 into the coronary sinus. The guide wire 13 is then distally extended beyond the inner sheath 1 into a branch of the coronary sinus. The guide wire 13 can then be used to guide a pacing lead 14 into the branch vessel. The pacing lead 14 is advanced through the inner sheath 1 and seated into the branch of the coronary sinus.

Figure 5:
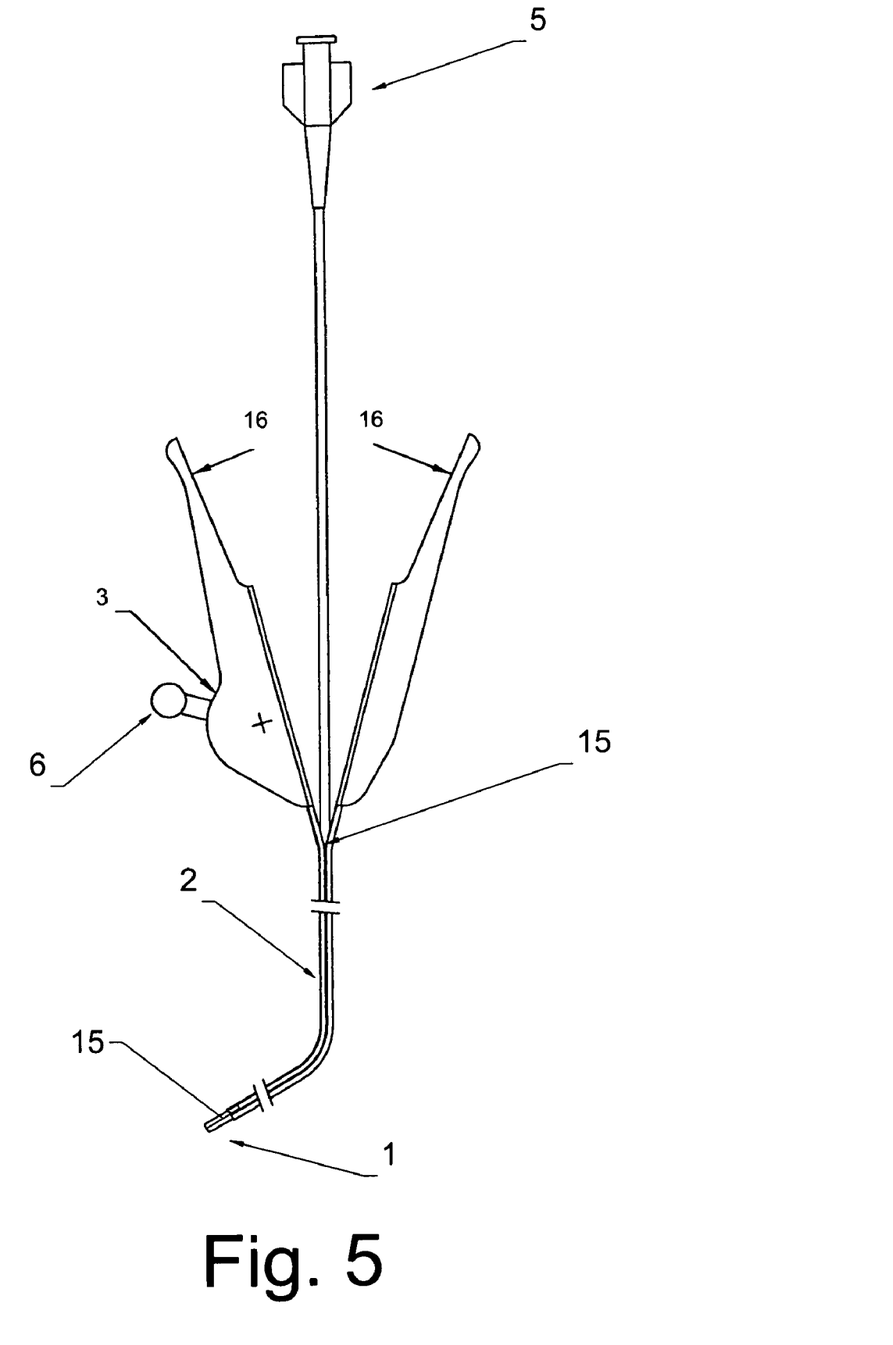
FIG. 5 is an external view of a catheter illustrating a peel-away outer sheath according to an embodiment of the present invention.

At this point in the procedure, it may be desired to remove at least the outer sheath 2. In one configuration, the outer sheath 2 can be made with a peel away feature. Turning to FIG. 5, a peel away feature may include one or more longitudinal pre-stress lines 15 extending from proximal to distal ends along the outer sheath 2. The advantages of a peel-away feature include the ability to proximally remove the outer sheath 2 over the inner sheath 1 seated without disturbing any proximal attachments on the inner sheath 1. Proximal attachments on the inner sheath 1 may include a wing luer 5.

A peel-away feature of the outer sheath 2 in a catheter according the present invention can further include the ability of the guide handle 3 to separate into at least two sections. As seen in FIG. 5, application of forces to the separation grips 16 can split the guide handle 3. The guide handle 3 is connected to the outer sheath 2, so guide handle separation can initiate outer sheath separation as well. Further details of exemplary peel-away features are disclosed in commonly owned U.S. application Ser. No. 10/036,640 entitled "Telescoping Guide Catheter With Peel-Away Outer Sheath", which is hereby incorporated herein by reference.

In some cases, it may be desirable to remove the inner sheath 1 prior to introducing the pacing lead 14. In such a case, the pacing lead 14 is advanced through the outer sheath 2. This may be desirable as the outer sheath lumen 2A is larger than that of the inner sheath 1. In this scenario, the outer sheath 2 is distally advanced over the inner sheath 1 until the outer sheath 2 is seated in the coronary sinus. The inner sheath 1 is then proximally retracted and removed, whereupon pacing lead insertion can proceed through the outer sheath 2.

Figure 6:
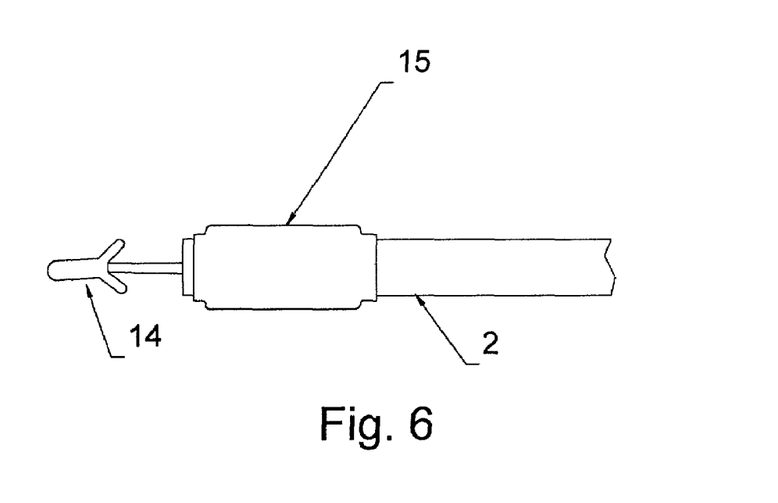
FIG. 6 is an external view of a catheter containing a pacing lead within the outer sheath according to an embodiment of the present invention.

This situation is illustrated in FIG. 6, where the pacing lead 14 is shown extending from the distal end of the outer sheath 2. The outer sheath 2 illustrated in FIG. 6 also employs a distally mounted occlusion balloon 15. The occlusion balloon 15 can be inflated when the outer sheath 2 is in a vessel where blockage of blood flow is desired. Blood flow can be temporarily occluded in this way before injecting a contrast media, for example. The occlusion balloon 15 is typically inflated by a fluid injected from a proximal end of the outer sheath 2. Methods of mounting and actuating the occlusion balloon 15 are well known in the art.

Figure 7:
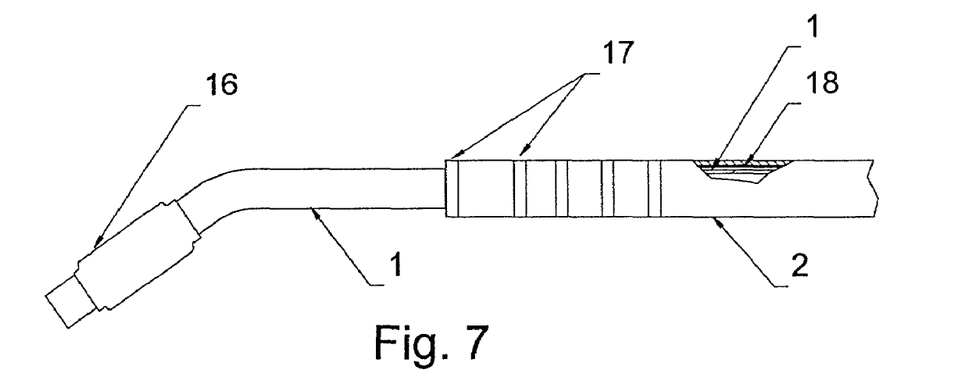
FIG. 7 is a view of the distal end of a catheter showing an occlusion balloon attached to the inner sheath according to an embodiment of the present invention.

FIG. 7 illustrates an occlusion balloon 16 mounted on the distal end of the inner sheath 1. Actuation and disposition of the occlusion balloon 16 is similar to that described for the occlusion balloon 15 mounted on the outer sheath 2.

Another useful configuration of a guide catheter according to the present invention includes attaching electrodes to a distal end of the guide catheter. FIG. 7 shows electrodes 17 mounted on the distal end of the outer sheath 2. The electrodes 17 are typically flush mounted, and are connected to at least one conductor 18 that is disposed between the distal and proximal ends of the inner sheath 1.

Figure 8:
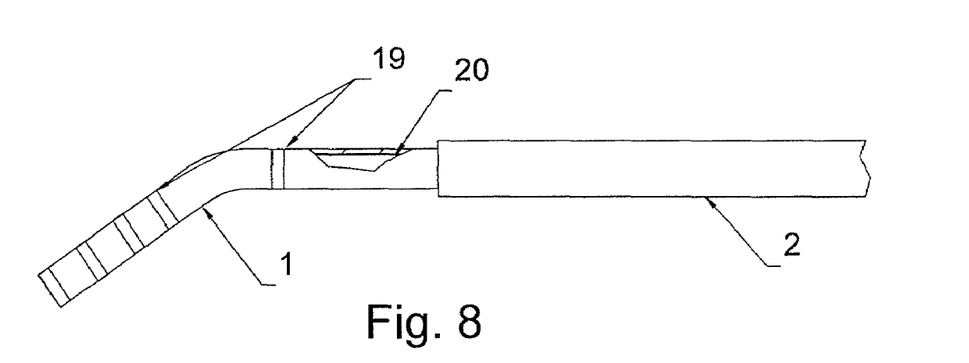
FIG. 8 is view of the distal end of a catheter illustrating electrodes on the distal tip of the inner sheath according to an embodiment of the present invention.

FIG. 8 shows electrodes 19 mounted on the inner sheath 1 in a similar fashion as the electrodes 17 on the outer sheath 2. The electrodes 19 are connected to at least one conductor 20 that is disposed within the inner sheath 1. It is understood the electrodes may be disposed on both the inner and outer sheaths 1, 2 in certain configurations.

The electrodes 17, 19 can be used for electrophysiological (EP) purposes, such as EP mapping structures within the heart. EP electrodes are often fabricated from stainless steel, although the electrodes 17, 19 could be made of platinum, silver or other electrode materials known in the art. A guide catheter according to the present invention can also be adapted to use ablation electrodes. Ablation electrodes are typically formed of platinum/iridium, and can be mounted as previously described and illustrated in FIGS. 7 and 8.

Another adaptation of a catheter according to the present invention includes attaching one or more pressure sensing devices to at least the distal end of the inner and/or outer sheaths 1, 2. A pressure sensor, for example, can detect dynamic characteristics of blood flow, including fluid velocity. Tubular piezoelectric sensors can be configured to sense pressure on the inner sheath 1, and can be deployed in a similar manner to the electrodes 19 shown in FIG. 8. As with the electrodes 19, at least one conductor 20 would be coupled to the pressure sensing device and disposed within the inner or outer sheath 1, 2. Other sensors that can be similarly incorporated on the inner and outer sheaths 1, 2 include a temperature sensor, activity sensor (e.g. accelerometer) or oxygen sensor.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A guide catheter, comprising:

an outer sheath comprising an open lumen, a pre-shaped distal end, a distal tip, a proximal end, and at least one longitudinally disposed pre-stress line extending from the proximal end to the distal tip of the outer sheath;

an inner sheath comprising an open lumen, the inner sheath disposed within the open lumen of the outer sheath, the inner sheath axially rotatable and longitudinally translatable relative to the outer sheath, a distal end of the inner sheath conforming to a shape of the outer sheath when the inner sheath is retracted, and the distal end of the inner sheath assuming a pre-formed shape different from the shape of the outer sheath when the distal end of the inner sheath is extended beyond the distal end of the outer sheath;

a steering tendon disposed along the outer sheath, a distal end of the steering tendon connected to the distal tip of the outer sheath;

a guide handle connected to the proximal end of the outer sheath, the guide handle comprising at least one longitudinally disposed pre-stress line aligned with the at least one longitudinally disposed pre-stressed line of the outer sheath, and at least two elongated separation grips positioned at the proximal end of the guide handle aligned substantially parallel to the at least one longitudinally disposed pre-stress line of the guide handle, the guide catheter configured such that separation of the guide handle into at least two sections along the at least one longitudinally disposed pre-stress line of the guide handle initiates separation of the outer sheath along the at least one pre-stress line of the outer sheath;

a steering mechanism comprising a lever pivotably disposed on the guide handle, the steering mechanism connected to a proximal end of the steering tendon and providing a pulling force on the steering tendon in response to pivoting of the lever to adjustably change a shape of the pre-shaped distal end of the outer sheath;

at least one pressure sensing device connected to the distal end of the inner sheath; and at least one electrical conductor coupled to the at least one pressure sensing device, the at least one conductor disposed within the inner sheath.

2. A guide catheter according to claim 1, wherein the lever of the steering mechanism comprises a steering handle.

3. A guide catheter according to claim 1, wherein the inner sheath further comprises at least one longitudinally disposed pre-stress line extending from a proximal end to a distal tip of the inner sheath.

4. A guide catheter according to claim 1, further comprising:
    at least one electrode on the distal end of the inner sheath; and
    at least one electrical conductor coupled to the at least one electrode, the at least one conductor disposed within the inner sheath.

5. A guide catheter according to claim 1, further comprising:
    at least one electrode on the pre-shaped distal end of the outer sheath; and
    at least one electrical conductor coupled to the at least one electrode, the at least one conductor disposed within the outer sheath.

6. A guide catheter according to claim 1, further comprising an occlusion device connected to the distal end of the inner sheath.

7. A guide catheter according to claim 1, further comprising an occlusion device connected to the pre-shaped distal end of the outer sheath.

8. A guide catheter according to claim 1, further comprising a retention mechanism provided on the guide handle to retain the steering lever at a fixed position.

9. A guide catheter according to claim 1, wherein the pre-shaped distal end of the outer sheath further comprises:
    a substantially straight section at the distal tip of the outer sheath having a length of about 1 cm to about 5 cm; and
    a substantially circular curve proximally adjacent to the straight section, the circular curve having a bend radius ranging from about 0 degrees to about 180 degrees and a bend radius ranging from about 1 cm to about 7 cm.

10. A guide catheter according to claim 1, wherein the pre-formed shape of the distal end of the inner sheath further comprises:
    a substantially straight section at the distal tip of the inner sheath having a length of about 0.5 cm to about 4.0 cm; and
    a substantially circular curve proximally adjacent to the straight section, the circular curve having a bend radius ranging from about 0 degrees to about 150 degrees and a bend radius ranging from about 1 cm to about 5 cm.

11. A guide catheter according to claim 1, wherein the steering tendon is disposed on an outer surface of the outer sheath.

12. A guide catheter according to claim 1, wherein the steering tendon is disposed within the open lumen of the outer sheath.

13. A guide catheter according to claim 1, wherein the outer sheath further comprises a second lumen, the steering tendon disposed within the second lumen of the outer sheath.

14. The guide catheter according to claim 1, wherein the retention mechanism comprises a locking arrangement configured to lock the steering lever at the fixed position.

15. The guide catheter according to claim 1, wherein the retention mechanism comprises an arrangement configured to frictionally retain the steering lever at the fixed position.

16. A guide catheter, comprising:
    an outer sheath comprising an open lumen, a pre-shaped distal end, a distal tip, a proximal end, and at least one longitudinally disposed pre-stress line extending from the proximal end to the distal tip of the outer sheath;
    an inner sheath comprising an open lumen configured to receive a payload, the inner sheath disposed within the open lumen of the outer sheath, the inner sheath rotatable and longitudinally displaceable relative to the outer sheath, a distal end of the inner sheath conforming to a shape of the outer sheath when the inner sheath is retracted, and the distal end of the inner sheath assuming a pre-formed shape different from the shape of the outer sheath when the distal end of the inner sheath is extended beyond the distal end of the outer sheath;
    a steering member disposed along the outer sheath, a distal end of the steering member connected to the distal tip of the outer sheath;
    a guide handle connected to the proximal end of the outer sheath, the guide handle comprising at least one longitudinally disposed pre-stress line aligned with the at least one longitudinally disposed pre-stressed line of the outer sheath and at least two elongated separation grips positioned at the proximal end of the guide handle aligned substantially parallel to the at least one longitudinally disposed pre-stress line of the guide handle, the guide catheter configured such that separation of the guide handle into at least two sections along the at least one longitudinally disposed pre-stress line of the guide handle initiates separation of the outer sheath along the at least one pre-stress line of the outer sheath;
    a steering mechanism comprising a lever pivotably disposed on the guide handle, the steering mechanism connected to a proximal end of the steering tendon and from which a pulling force is developed on the steering tendon in response to pivoting of the lever to adjustably change a shape of the pre-shaped distal end of the outer sheath;
    at least one pressure sensing device connected to the pre-shaped distal end of the outer sheath; and
    at least one electrical conductor coupled to the at least one pressure sensing device, the at least one conductor disposed within the outer sheath.

17. The guide catheter of claim 16, wherein the payload comprises a cardiac lead.

18. The guide catheter of claim 16, wherein the payload comprises a cardiac lead configured for implantation with a coronary sinus or a branch vessel of the coronary sinus.

19. The guide catheter of claim 16, wherein the payload comprises a pacing lead.

20. The guide catheter of claim 16, wherein the payload comprises a defibrillation lead.

21. The guide catheter of claim 16, wherein the payload comprises an injectable media.

22. The guide catheter of claim 16, wherein the payload comprises a guide wire.

23. The guide catheter of claim 16, wherein the payload comprises a guide wire and a cardiac lead having a lumen dimensioned to receive the guide wire, the lumen of the cardiac lead dimensioned to permit displacement of the cardiac lead over the guide wire.

24. The guide catheter of claim 16, wherein the inner sheath further comprises at least one longitudinally disposed pre-stress line extending from a proximal end to a distal tip of the inner sheath.

25. The guide catheter of claim 16, further comprising:
    at least one electrode on the distal end of the inner sheath; and at least one electrical conductor coupled to the at least one electrode, the at least one conductor disposed within the inner sheath.

26. The guide catheter of claim 16, further comprising:
at least one electrode on the pre-shaped distal end of the outer sheath; and
at least one electrical conductor coupled to the at least one electrode, the at least one conductor disposed within the outer sheath.

27. The guide catheter of claim 16, further comprising an occlusion device connected to the distal end of the inner sheath.

28. The guide catheter of claim 16, further comprising an occlusion device connected to the pre-shaped distal end of the outer sheath.

29. The guide catheter of claim 16, further comprising a retention mechanism provided on the guide handle to retain the steering lever at a fixed position.

30. The guide catheter of claim 16, wherein:
the pre-shaped distal end of the outer sheath further comprises:
a substantially straight section at the distal tip of the outer sheath having a length of about 1 cm to about 5 cm; and
a substantially circular curve proximally adjacent to the straight section, the circular curve having a bend radius ranging from about 0 degrees to about 180 degrees and a bend radius ranging from about 1 cm to about 7 cm; and
the pre-formed shape of the distal end of the inner sheath further comprises:
a substantially straight section at the distal tip of the inner sheath having a length of about 0.5 cm to about 4.0 cm; and
a substantially circular curve proximally adjacent to the straight section, the circular curve having a bend radius ranging from about 0 degrees to about 150 degrees and a bend radius ranging from about 1 cm to about 5 cm.

31. The guide catheter of claim 16, wherein the steering tendon is disposed on an outer surface of the outer sheath or within the open lumen of the outer sheath.

32. The guide catheter of claim 16, wherein the outer sheath further comprises a second lumen, the steering tendon disposed within the second lumen of the outer sheath.

33. The guide catheter according to claim 16, wherein the retention mechanism comprises a locking arrangement configured to lock the steering lever at the fixed position.

34. The guide catheter according to claim 16, wherein the retention mechanism comprises an arrangement configured to frictionally retain the steering lever at the fixed position.

* * * * *